(12) United States Patent
Tsujimoto

(10) Patent No.: US 10,114,003 B2
(45) Date of Patent: Oct. 30, 2018

(54) STEM CELL DIFFERENTIATION DETERMINATION DEVICE, METHOD, AND PROGRAM

(71) Applicant: FUJIFILM Corporation, Tokyo (JP)

(72) Inventor: Takayuki Tsujimoto, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 149 days.

(21) Appl. No.: 15/045,848

(22) Filed: Feb. 17, 2016

(65) Prior Publication Data
US 2016/0161464 A1    Jun. 9, 2016

Related U.S. Application Data

(63) Continuation of application No. PCT/JP2014/004204, filed on Aug. 18, 2014.

(30) Foreign Application Priority Data

Aug. 22, 2013  (JP) ................. 2013-172378

(51) Int. Cl.
*G06K 9/00* (2006.01)
*G01N 33/483* (2006.01)
*C12M 1/34* (2006.01)

(52) U.S. Cl.
CPC ......... *G01N 33/4833* (2013.01); *C12M 41/36* (2013.01); *C12M 41/46* (2013.01)

(58) Field of Classification Search
CPC .... G01N 33/4833; C12M 41/36; C12M 41/46
See application file for complete search history.

(56) References Cited

U.S. PATENT DOCUMENTS 8,977,031 B2 *  3/2015  Watakabe .............. C12M 41/46
                                                              382/133
2007/0037199 A1  2/2007  Takahashi et al.
(Continued)

FOREIGN PATENT DOCUMENTS

JP    2007-006720 A    1/2007
JP    2008-182993 A    8/2008
(Continued)

OTHER PUBLICATIONS

International Search Report of PCT/JP2014/004204, dated Nov. 25, 2014. [PCT/ISA/210].
(Continued)

*Primary Examiner* — John Strege
(74) *Attorney, Agent, or Firm* — Sughrue Mion, PLLC

(57) ABSTRACT

A stem cell differentiation determination device includes an observation image acquisition unit that captures an image of an observation region including a stem cell in time series to acquire at least two observation images, a feature amount acquisition unit that acquires at least one feature amount of the stem cell for each observation image, a determination unit that determines whether or not the stem cell has been differentiated, on the basis of the feature amount, a change information acquisition unit that acquires information about a change in the feature amount between the observation images captured in time series or information about a change in a determination result from undifferentiation to differentiation between the observation images, and an output unit that outputs the information about a change in the feature amount or the information about a change in the determination result.

14 Claims, 3 Drawing Sheets

(56) References Cited

U.S. PATENT DOCUMENTS

| | | | |
|---|---|---|---|
| 2010/0002929 A1* | 1/2010 | Sammak | G06K 9/00127 |
| | | | 382/133 |
| 2010/0255468 A1 | 10/2010 | Maeda et al. | |
| 2011/0019897 A1* | 1/2011 | Takagi | G06T 7/0012 |
| | | | 382/133 |
| 2011/0188728 A1* | 8/2011 | Sammak | G06K 9/00 |
| | | | 382/133 |
| 2011/0235899 A1 | 9/2011 | Tanaka | |
| 2012/0087556 A1* | 4/2012 | Dai | G06K 9/0014 |
| | | | 382/128 |
| 2012/0092478 A1 | 4/2012 | Honda et al. | |
| 2012/0315620 A1* | 12/2012 | Watakabe | G01N 33/5073 |
| | | | 435/3 |
| 2014/0064594 A1 | 3/2014 | Sugiyama et al. | |
| 2014/0073002 A1* | 3/2014 | Yamauchi | G01N 15/1456 |
| | | | 435/34 |

FOREIGN PATENT DOCUMENTS

| | | |
|---|---|---|
| JP | 2009-44974 A | 3/2009 |
| JP | 2010-128820 A | 6/2010 |
| JP | 2011-229409 A | 11/2011 |
| JP | 2011-229410 A | 11/2011 |
| JP | 2011-229411 A | 11/2011 |
| JP | 4852890 B2 | 1/2012 |
| JP | 2012-95627 A | 5/2012 |
| WO | 2010/098105 A1 | 9/2010 |
| WO | 2012/115153 A1 | 8/2012 |
| WO | 2012/147403 A1 | 11/2012 |

OTHER PUBLICATIONS

Written Opinion of PCT/JP2014/004204, dated Nov. 25, 2014. [PCT/ISA/237].
Communication dated Sep. 6, 2016 from the Japanese Patent Office in counterpart application No. 2013-172378.

* cited by examiner

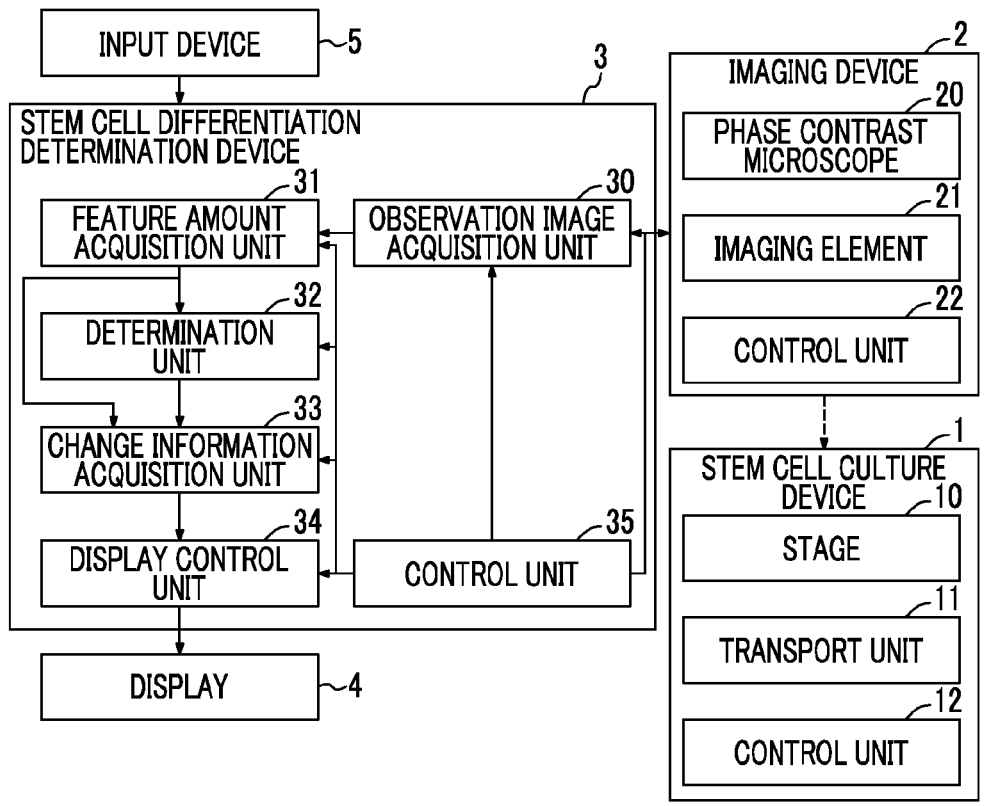

)# STEM CELL DIFFERENTIATION DETERMINATION DEVICE, METHOD, AND PROGRAM

CROSS REFERENCE TO RELATED APPLICATIONS

The present application is a Continuation of PCT International Application No. PCT/JP2014/004204 filed on Aug. 18, 2014, which claims priority under 35 U.S.C. § 119(a) to Japanese Patent Application No. 2013-172378 filed on Aug. 22, 2013. Each of the above applications is hereby expressly incorporated by reference in its entirety, into the present application.

BACKGROUND OF THE INVENTION

1. Field of the Invention

The present invention relates to a stem cell differentiation determination device and method and a program which determine whether a stem cell has been differentiated on the basis of an observation image obtained by capturing an image of an observation region including a stem cell.

2. Description of the Related Art

A stem cell, such as an ES cell or an iPS cell, has the capability to be differentiated to cells of various tissues and has drawn attention since it can be applied to, for example, regenerative medicine, the development of drugs, and the interpretation of disease.

The stem cell is seeded in a culture medium in a culture container which is provided in a cell culture device and is multiplied in the culture medium. Stem cell colonies are grown while adjacent stem cell colonies are repeatedly combined with each other.

It is necessary to multiply the stem cell while maintaining the stem cell in an undifferentiated state, in order to improve differentiation efficiency when the stem cell is differentiated to a cell of a target tissue in the growth process of the stem cell. Therefore, once the stem cell starts to be differentiated, it is difficult to grow the stem cell to a target tissue.

There is a technique which cuts out only the region which is likely to be undifferentiated in a stem cell colony and transplants the cut region to another culture container to perform subculturing. However, when the subculturing is performed, it is necessary to extract only the undifferentiated stem cell. That is, when the stem cell is cultured, it is necessary to appropriately determine the differentiation and undifferentiation of the stem cell.

For example, JP2012-95627A and JP2011-229410A disclose a technique which captures an image of a stem cell over time, checks a change in the observation image over time, and determines the undifferentiation and differentiation of the stem cell.

WO2012/147403A and JP2009-44974A disclose a technique which acquires various feature amounts of a stem cell colony that is being cultured and determines the undifferentiation and differentiation of each colony on the basis of the feature amounts.

JP4852890B discloses a technique which determines the undifferentiation and differentiation of a stem cell, using tens of types of feature amounts including, for example, the number of stem cells and the number of nucleoli.

SUMMARY OF THE INVENTION

However, when the culturist observes the observation image of the stem cell that is being cultured and determines the undifferentiation and differentiation of the stem cell as in JP2012-95627A and JP2011-229410A, it is difficult for the culturist to determine the imaging time of the observation image in which the stein cell has changed from an undifferentiated state to a differentiated state. Therefore, the culturist needs to check the observation images captured at all times and to specify the position where the state of the stem cell has changed, which is inefficient.

When the undifferentiation and differentiation of each colony are determined as in WO2012/147403A and JP2009-44974A, it takes a great deal of time for the culturist to check all of the colonies or the culturist selects a random colony and checks the selected colony, The former is inefficient and the latter is not an appropriate checking method since non-uniformity occurs in each colony even under the same culture conditions.

JP4852890B discloses a technique which determines the undifferentiation and differentiation of the stem cell on the basis of various feature amounts. However, when the culturist checks the determination result of undifferentiation and differentiation, it is difficult for the culturist to check which of the feature amounts is used to obtain the determination result and there is a problem that the interpretation of the determination result by the culturist depends on the skill level of the culturist.

The invention has been made in view of the above-mentioned problems and an object of the invention is to provide a stem cell differentiation determination device and method and a program which enable a culturist to effectively and accurately check undifferentiation and differentiation.

According to an aspect of the invention, there is provided a stem cell differentiation determination device including: an observation image acquisition unit that captures an image of an observation region including a stem cell in time series to acquire at least two observation images; a feature amount acquisition unit that acquires at least one feature amount of the stem cell for each observation image; a determination unit that determines whether or not the stem cell has been differentiated, on the basis of the feature amount; a change information acquisition unit that acquires information about a change in the feature amount between the observation images captured in time series or information about a change in a determination result from undifferentiation to differentiation between the observation images; and an output unit that outputs the information about a change in the feature amount or the information about a change in the determination result.

In the stem cell differentiation determination device according to the above-mentioned aspect, the change information acquisition unit may acquire, as the information about a change in the feature amount, at least one of information about a time when the feature amount changes, the observation image in which the feature amount has changed, information about a position where the feature amount has changed in the observation region, and information for specifying a stem cell colony in which the feature amount has changed.

In the stem cell differentiation determination device according to the above-mentioned aspect, the change information acquisition unit may acquire, as the information about a change in the determination result, at least one of information about a time when the determination result changes, the observation image in which the determination result has changed, information about a position where the determination result has changed in the observation region, and information for specifying a stem cell colony in which the determination result has changed.

The feature amount acquisition unit may acquire the feature amount for each of a plurality of regions in the observation region and the determination unit may perform the determination for each region. The stem cell differentiation determination device according to the above-mentioned aspect of the invention may further include a reliability acquisition unit that acquires reliability of the determination result for each region, on the basis of the feature amount for each region. The output unit may preferentially output the observation image including the region with low reliability.

The region may be a stem cell colony region.

The region may be a predetermined divided region.

The output unit may output the feature amount.

The stem cell differentiation determination device according to the above-mentioned aspect of the invention may further include an imaging unit that captures the observation image. The imaging unit may switch an optical magnification or a resolution when the observation image is captured, depending on a set feature amount of interest.

The output unit may output the observation image of the entire stem cell colony.

The output unit may output the observation image of a portion of the stem cell colony.

The output unit may output a plurality of observation images, which are captured before and after the time when the feature amount changes or the time when the determination result changes, as a moving image.

According to another aspect of the invention, there is provided a stem cell differentiation determination method including: capturing an image of an observation region including a stem cell in time series to acquire at least two observation images; acquiring at least one feature amount of the stem cell for each observation image; determining whether or not the stem cell has been differentiated, on the basis of the feature amount; and acquiring information about a change in the feature amount between the observation images captured in time series or information about a change in a determination result from undifferentiation to differentiation between the observation images, and outputting the information about a change in the feature amount or the information about a change in the determination result.

According to another aspect of the invention, there is provided a stem cell differentiation determination program that causes a computer to function as: an observation image acquisition unit that captures an image of an observation region including a stem cell in time series to acquire at least two observation images; a feature amount acquisition unit that acquires at least one feature amount of the stem cell for each observation image; a determination unit that determines whether or not the stem cell has been differentiated, on the basis of the feature amount; a change information acquisition unit that acquires information about a change in the feature amount between the observation images captured in time series or information about a change in a determination result from undifferentiation to differentiation between the observation images; and an output unit that outputs the information about a change in the feature amount or the information about a change in the determination result.

In the stem cell differentiation determination device and method and the program according to the invention, the image of the observation region including the stem cell is captured in time series to acquire at least two observation images. At least one feature amount of the stem cell is acquired for each observation image. It is determined whether or not the stem cell has been differentiated, on the basis of the feature amount. The information about a change in the feature amount between the observation images captured in time series or the information about a change in the determination result from undifferentiation to differentiation between the observation images are acquired. The information about a change in the feature amount or the information about a change in the determination result is output. Therefore, it is possible to limit the information to be checked by the culturist, which makes it possible for the culturist to effectively and accurately check undifferentiation and differentiation.

BRIEF DESCRIPTION OF THE DRAWINGS

FIG. 1 is a block diagram schematically illustrating the structure of a stem cell culture observation system using a first embodiment of a stem cell differentiation determination device according to the invention.

FIG. 2 is a diagram illustrating an example of a table in which the feature amounts of interest are associated with a magnification and a resolution.

DESCRIPTION OF THE PREFERRED EMBODIMENTS

Figure 3:
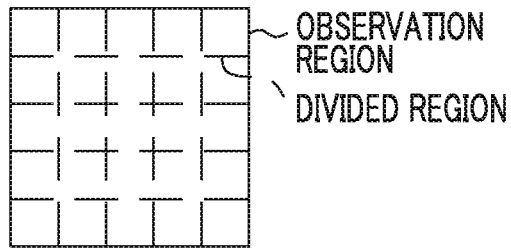
FIG. 3 is a diagram illustrating an example of a divided region obtained by dividing an observation region.

Hereinafter, a first embodiment of a stem cell differentiation determination device and method and a program according to the invention will be described in detail with reference to the drawings. The invention is characterized in, for example, the output of the change information of observation images obtained by capturing an image of a stem cell in time series. First, the overall structure of a stem cell culture observation system including the stein cell differentiation determination device will be described. FIG. 1 is a block diagram schematically illustrating the structure of the stem cell culture observation system, As illustrated in FIG. 1, the stem cell culture observation system includes a stem cell culture device 1, an imaging device 2, a stem cell differentiation determination device 3, a display 4, and an input device 5.

The stem cell culture device 1 is used to culture stem cells. The stem cell culture device 1 includes a plurality of culture containers in which the cells to be cultured are seeded in a culture medium. The stem cell culture device 1 includes a stage 10, a transport unit 11, and a control unit 12.

The culture container of which the image is to be captured by the imaging device 2 is placed on the stage 10. The transport unit 11 selects the culture container of which the image is to be captured from a plurality of culture containers which are accommodated at predetermined positions in the stem cell culture device 1 and transports the selected culture container to the stage 10. The control unit 12 controls the overall operation of the stem cell culture device 1 and controls environmental conditions, such as temperature, humidity, and $CO_2$ concentration, in the stem cell culture device 1, in addition to the operation of the stage 10 or the transport unit 11. A known structure can be used to adjust the temperature, humidity, and $CO_2$ concentration.

The imaging device 2 captures the observation image of an observation region including the stem cell in the culture container placed on the stage 10. The imaging device 2 includes an optical system 20 which forms and acquires the observation image, an imaging element 21 which converts the observation image formed by the optical system 20 into an electric signal and outputs the electric signal as an image signal, and a control unit 22 which controls the optical system 20 and the imaging element 21.

For example, a phase contrast microscope or a differential interference microscope can be used as the optical system 20. In addition, for example, a complementary metal-oxide semiconductor (CMOS) sensor or a charge-coupled device (CCD) sensor can be used as the imaging element 21.

The control unit 22 controls the overall operation of the imaging device 2. In particular, in this embodiment, the control unit 22 controls the magnification of the optical system 20 or the resolution of the imaging element 21.

Specifically, in this embodiment, the control unit 22 changes the magnification or the resolution, depending on the feature amounts of interest which are used to determine whether or not the stem cell has been differentiated in the stem cell differentiation determination device 3.

For example, a table illustrated in FIG. 2 in which the feature amounts of interest are associated with the magnification and the resolution is set in the control unit 22. Before the observation image of the stem cell is captured, the user uses the input device 5 to input the feature amounts of interest. The feature amounts which are input by the user are set in the determination unit 32 of the stem cell differentiation determination device 3 and are input to the control unit 22 of the imaging device 2 through a control unit 35 of the stem cell differentiation determination device 3. The control unit 22 sets the magnification of the optical system 20 and the resolution of the imaging element 21 on the basis of the input feature amounts, with reference to the table.

In the table illustrated in FIG. 2, when the feature amount of interest is the degree of circularity of a colony, a relatively low magnification (4 times) and a low resolution (340 pixels×256 pixels) are set. When the feature amount of interest is the density of stem cells, a relatively high magnification (20 times) and a high resolution (1360 pixels× 1024 pixels) are set. The reason is as follows. When the degree of circularity of the colony is acquired as the feature amount, it is preferable that the magnification is low since it is necessary to check the entire colony. In addition, since only the outward shape of the colony is distinguished, a very high resolution is not required. When the density of the stem cells is acquired as the feature amount, it is necessary to distinguish the stem cells in the colony. Therefore, it is preferable that the magnification and the resolution are high.

For a change in the resolution, for example, a plurality of imaging elements 21 with different resolutions may be switched or binning may be performed for down-sampling when an image signal is read from one imaging element 21.

When both the degree of circularity of the colony and the density of the stem cells are acquired as the feature amounts, the observation image may be captured while the magnification and the resolution are switched. In addition, magnifications and resolutions different from the magnification and the resolution illustrated in FIG. 2 may be stored in the table and the magnification and the resolution may be set.

The feature amounts which are used to determine whether or not the stem cell has been differentiated in the stem cell differentiation determination device 3 may be switched according to the maturity of the stem cell, and the magnification and resolution of the imaging device 2 may be set on the basis of the feature amounts corresponding to the maturity. Specifically, for example, in a case in which the stem cell has not been grown to form a colony, when the undifferentiation and differentiation of the stem cell are determined on the basis of the outward shape of a stem cell colony, the accuracy of the determination is likely to be reduced. In this stage, when the stem cells have not been differentiated, the distribution of the stem cells is uniform. When some of the stem cells have been differentiated, the distribution of the stem cells is not uniform. Therefore, preferably, the uniformity of the stem cells is set as the feature amount of interest and the magnification and resolution of the imaging device 2 are set to values corresponding to the uniformity of the stem cells. Specifically, for example, the magnification and the resolution are set to values greater than those when the degree of circularity of the colony is evaluated, as illustrated in FIG. 2.

In a stage in which the maturity of the stem cell is sufficiently high to form a colony, the stem cell differentiation determination device 3 may set the feature amounts of interest to the degree of circularity of the colony and the density of the stem cells, the magnification and resolution of the imaging device 2 may be set to values corresponding to the degree of circularity of the colony and the density of the stem cells, and the observation image may be captured at the magnification and the resolution. Specifically, for example, when an observation image for evaluating the degree of circularity of the colony is captured, the magnification and the resolution may be set to relatively small values and the observation image may be captured at the set magnification and resolution. When an observation image for evaluating the density of the stem cells is captured, the magnification and the resolution may be set to relatively large values and the observation image may be captured at the set magnification and resolution.

In a stage in which the maturity of the stem cells increases and colonies start to be combined with each other, the determination of undifferentiation and differentiation based on the degree of circularity of the colony is likely to cause a determination error. Therefore, in this stage, the density of the stem cells may be set as the feature amount of interest and the magnification and resolution of the imaging device 2 may be set to values corresponding to the density of the stem cells. Specifically, for example, the magnification and the resolution are set to relatively large values even when the degree of circularity of the colony is evaluated, as described above.

For the maturity of the stem cell, for example, a timer may be provided and the elapsed time which is measured by the timer may be acquired as the maturity. Alternatively, the number of stem cells in the observation image may be counted and the count value may be acquired as the maturity.

An embodiment of a stem cell differentiation determination program according to the invention is installed in a computer to implement the stem cell differentiation determination device 3.

The stem cell differentiation determination device 3 includes, for example, a central processing unit, a semiconductor memory, and a hard disk and an embodiment of the stem cell differentiation determination program is installed in the hard disk. When the control unit 35 including a central processing unit executes the program, an observation image acquisition unit 30, a feature amount acquisition unit 31, a determination unit 32, a change information acquisition unit 33, and a display control unit 34 illustrated in FIG. 1 operate. In this embodiment, the display control unit corresponds to an output unit. However, the function of the output unit is not limited to a display control function. For example, the output unit may output information to be recorded on other devices.

The observation image acquisition unit 30 acquires a plurality of observation images which are captured in time series by the imaging device 2 and stores the acquired observation images. In addition, the observation image acquisition unit 30 outputs the acquired observation images to the feature amount acquisition unit 31 and the display control unit 34.

The feature amount acquisition unit 31 acquires at least one feature amount of the stem cell for each of the time-series observation images acquired by the observation image acquisition unit 30. The feature amounts of the stem cell include, for example, the degree of circularity of a stem cell colony, the density of stem cells, and the uniformity of stem cells.

The feature amounts are not limited thereto and other feature amounts may be acquired. For example, whether or not a defect, such as a hole, is present in the colony may be acquired as the morphological feature amount of the colony. When a defect is present in the colony, it is considered that the stem cell has been differentiated.

For the degree of circularity of the colony or the defect in the colony, the observation image may be binarized and labeled and the feature amount may be acquired from the observation image. For the density of stem cells or the uniformity of stem cells, the edge of the observation image may be detected using, for example, a Sobel filter and the density or uniformity of the edge may be calculated to acquire the feature amount.

In addition, both the uniformity of stem cells and the degree of circularity of the colony may be acquired as the feature amounts, weights on the feature amounts may be changed depending on the maturity of the stem cell, and the evaluation value may be acquired. Specifically, for example, a weight on the uniformity of the stem cells may be greater than a weight on the degree of circularity of the colony in a stage in which maturity does not increase and the weight on the degree of circularity of the colony may be greater than the weight on the uniformity of the stem cells in a stage in which maturity reaches a certain level.

Furthermore, the feature amounts corresponding to culture conditions may be acquired and the above-mentioned weights may be changed depending on the culture conditions. Specifically, for example, when a colony is seeded in a culture medium and is then cultured, the degree of circularity of the colony may be acquired as the feature amount. When only stem cells are seeded in a culture medium and are then cultured, for example, the density or uniformity of the stem cells may be acquired as the feature amount.

For example, in the case of the colony seeding, a weight on the degree of circularity of the colony may be greater than a weight on the density of the stem cells. In the case of the stem cell seeding, the weight on the density of the stem cells may be greater than the weight on the degree of circularity of the colony. The culture conditions are input by the user through the input device 5.

The feature amount acquisition unit 31 according to this embodiment acquires the feature amounts or the evaluation values for each stem cell colony in the observation image. Each stem cell colony can be detected by, for example, a method which detects the edge of the stem cell colony from the observation image and performs pattern matching for the detected edge. In the stage in which each stem cell is seeded and the maturity of each stem cell is not high enough to clearly form a stem cell colony, for example, the observation region may be divided into a plurality of predetermined regions and the feature amounts may be acquired for each divided region, as illustrated in FIG. 3.

The determination unit 32 determines whether or not the stem cell in the observation image has been differentiated, on the basis of the feature amount or the evaluation value for each stem cell colony or each divided region which is acquired by the feature amount acquisition unit 31. Specifically, when the degree of circularity of the colony is acquired as the feature amount, the determination unit 32 compares the degree of circularity with a predetermined threshold value. When the degree of circularity is equal to or greater than the threshold value, the determination unit 32 determines that the stem cell has not been differentiated. When the degree of circularity is less than the threshold value, the determination unit 32 determines that the stem cell has been differentiated.

When the density of the stem cells is acquired as the feature amount, the determination unit 32 compares the density of the stem cells with a predetermined threshold value. When the density is equal to or greater than the threshold value, the determination unit 32 determines that the stem cell has not been differentiated. When the density is less than the threshold value, the determination unit 32 determines that the stem cell has been differentiated.

When the uniformity of the stem cells is acquired as the feature amount, the determination unit 32 compares the uniformity of the stem cells with a predetermined threshold value. When the uniformity is equal to or greater than the threshold value, the determination unit 32 determines that the stem cell has not been differentiated. When the uniformity is less than the threshold value, the determination unit 32 determines that the stem cell has been differentiated.

In the case in which a defect in the colony is acquired as the feature amount, when there is no defect in the colony, the determination unit 32 determines that the stem cell has not been differentiated. When there is a defect in the colony, the determination unit 32 determines that the stem cell has been differentiated.

The determination method based on each feature amount has been descried above. However, for example, when a plurality of feature amounts are acquired, it may be determined whether or not the stem cell has been differentiated on the basis of at least one of the plurality of feature amounts. When it is determined that the stem cell has been differentiated, the final determination result indicating that the stem cell has been differentiated may be acquired. It may be determined whether or not the stem cell has been differentiated on the basis of some of the plurality of feature amounts. When it is determined that the stem cell has been differentiated, the final determination result indicating that the stem cell has been differentiated may be acquired. It may be determined whether or not the stem cell has been differentiated on the basis of all of the plurality of feature amounts. When it is determined that the stem cell has been differentiated, the final determination result indicating that the stem cell has been differentiated may be acquired. In addition, when a plurality of feature amounts are weighted to calculate the evaluation value, the evaluation value may be compared with a predetermined threshold value to determine whether or not the stem cell has been differentiated.

The change information acquisition unit 33 acquires information about a change in the feature amount between the observation image captured in time series or information about a change in the determination result from undifferentiation to differentiation between the observation images.

Specifically, for example, the change information acquisition unit 33 acquires, as the information about a change in the feature amount, at least one of information about the time when the feature amount changes, an observation image in which the feature amount has changed, information about a position where the feature amount has changed in the observation region, and information for specifying a stem cell colony in which the feature amount has changed.

The information about the time when the feature amount changes is, for example, the imaging time when the degree of circularity of at least one stem cell colony in the observation image is equal to or greater than a threshold value or the imaging time when the density of stem cells in at least one stem cell colony is equal to or greater than a threshold value. However, the information about the time is not limited to the imaging time when the feature amount is greater than the threshold value. For example, the imaging time when the amount of change in the feature amount is equal to or greater than a predetermined value may be acquired.

When other feature amounts or evaluation values are acquired for each stem cell colony or each divided region, the imaging time when the feature amounts or the evaluation values change from a value indicating the determination of undifferentiation to a value indicating the determination of differentiation may be acquired as the information about the time when the feature amount changes, or the imaging time when the feature amounts or the evaluation values are equal to or more than a predetermined amount of change may be acquired.

When a plurality of feature amounts or evaluation values are acquired for one stem cell colony or one divided region, the imaging time when at least one of the values changes may be acquired, or the latest imaging time among the imaging times when a predetermined number of values among the plurality of values change may be acquired as the time information when the feature amount changes. Alternatively, the latest imaging time among the imaging times when all of the plurality of values change may be acquired as the time information when the feature amount changes.

The observation image in which the feature amount has changed is an observation image which is captured at the time when the feature amount changes. In addition, the following may be acquired as the observation image in which the feature amount has changed: only an observation image captured at the imaging time when the feature amount changes; and the observation image captured at the imaging time when the feature amount changes and an observation image captured at the previous time.

Figure 4:
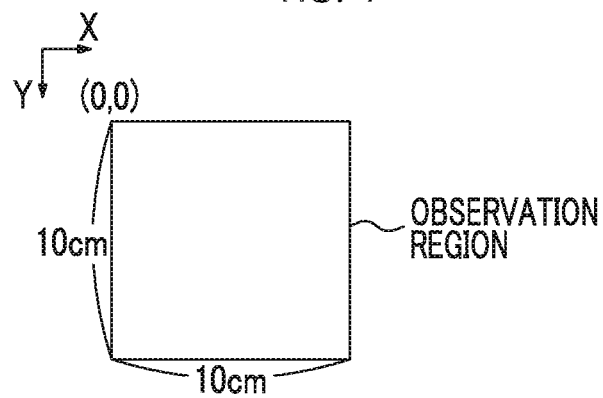
FIG. 4 is a diagram illustrating an example of the observation region.

The information about the position where the feature amount has changed in the observation region is, for example, information about the position of the stem cell colony or the divided region in which the feature amount or the evaluation value has changed in the observation region, as described above. A coordinate value in the observation region is acquired as the positional information. In this embodiment, as illustrated in FIG. 4, it is assumed that a rectangular region with a size of 10 cm×10 cm which is located in the vicinity of the center of the culture container is the observation region and coordinates are allocated, using the upper left corner point of the observation region as a coordinate value (0, 0). For example, the coordinate value of the center of the stem cell colony or the coordinate value of the center of gravity thereof is acquired as the coordinate value of the stem cell colony. In addition, the coordinate value of the center of the divided region or the coordinate value of the center of gravity thereof is acquired as the coordinate value of the divided region.

The information for specifying a stem cell colony is, for example, the number of the stem cell colony in which the feature amount or the evaluation value has changed when numbers are given to the stem cell colonies in the observation region.

In the above description, the change information acquisition unit 33 acquires the information about a change in the feature amount. However, information about a change in the determination result of the determination unit 32 from undifferentiation to differentiation may be acquired.

Specifically, the change information acquisition unit 33 may acquire, as the information about a change in the determination result, at least one of information about the time when the determination result changes, an observation image in which the determination result has changed, information about a position where the determination result has changed in the observation region, and information for specifying a stem cell colony in which the determination result has changed.

The information about the time when the determination result changes is, for example, the imaging time when the determination result of at least one stem cell colony or at least one divided region in the observation image changes from undifferentiation to differentiation.

The observation image in which the determination result has changed is an observation image which is captured at the time when the feature amount changes. In addition, the following may be acquired as the observation image in which the feature amount has changed: only an observation image captured at the imaging time when the determination result changes; and the observation image captured at the imaging time when the determination result changes and an observation image captured at the previous time.

The information about the position where the determination result has changed in the observation region is, for example, information about the position of the stem cell colony or the divided region in which the determination result has changed from undifferentiation to differentiation in the observation region.

The information for specifying a stem cell colony in which a determination result has changed is, for example, the number of the stem cell colony in which the determination result has changed from undifferentiation to differentiation when numbers are given to the stem cell colonies in the observation region.

When the change information acquisition unit 33 acquires the information about a change in the feature amount, the display control unit 34 displays the information about a change in the feature amount on the display 4, That is, the display control unit 34 displays, on the display 4, at least one of the information about the time when the feature amount changes, the observation image in which the feature amount has changed, the information about the position where the feature amount has changed in the observation region, and the information for specifying the stem cell colony in which the feature amount has changed.

When the change information acquisition unit 33 acquires the information about a change in the determination result, the display control unit 34 displays the information about a change in the determination result on the display 4. That is, the display control unit 34 displays, on the display 4, at least one of the information about the time when the determination result changes, the observation image in which the determination result has changed, the information about the position where the determination result has changed in the observation region, and the information for specifying the stem cell colony in which the determination result has changed.

When the information about the position where the feature amount or the determination result has changed in the observation region is displayed on the display 4, the display control unit 34 may mark and highlight the stem cell colony or the divided region in the positional information so as to be instantly distinguished, or may display a color map in which different colors are allocated to the stem cell colony or the divided region in the positional information and other stem cell colonies or divided regions. When the information for specifying the stem cell colony in which the feature amount or the determination result has changed is displayed, the display control unit 34 may mark and highlight the stem cell colony so as to be instantly distinguished, or may display a color map in which different colors are allocated to the stem cell colony and other stem cell colonies.

The input device 5 includes, for example, a mouse or a keyboard and receives an operation input by the user. For example, the input device 5 can receive the input of the feature amount of interest which is set when the optical magnification of the optical system 20 or the resolution of the imaging element 21 is determined. When the observation image is divided into a plurality of regions and the feature amount or the determination result is acquired for each divided region, the input device 5 can receive the input of the set range of the divided region.

Figure 5:
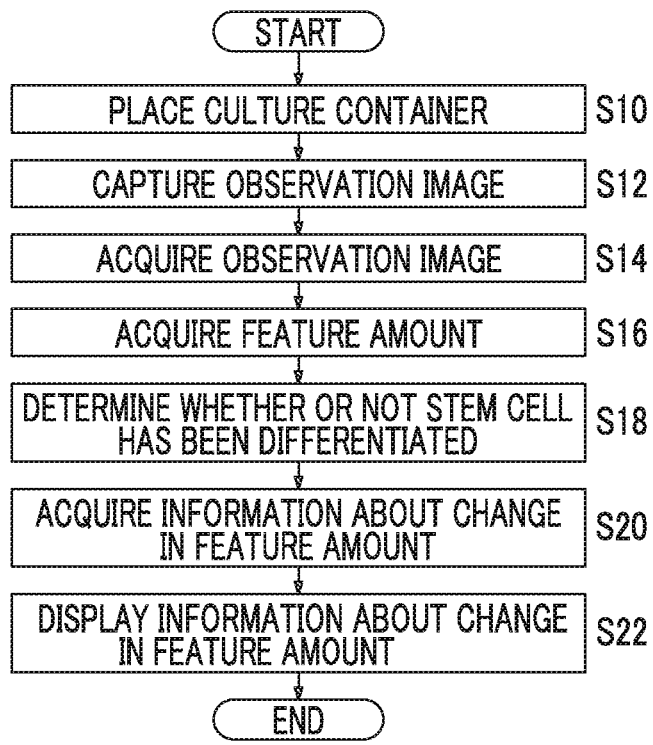
FIG. 5 is a flowchart illustrating the operation of the stem cell culture observation system illustrated in FIG. 1.

Next, the operation of the stem cell culture observation system will be described with reference to the flowchart illustrated in FIG. 5.

First, in the stem cell culture device 1, the transport unit 11 selects the culture container of which the image is to be captured from a plurality of culture containers provided in the stem cell culture device 1 and the selected culture container is placed on the stage 10 (S10).

Then, the observation image of an observation region including the stem cell in the culture container is captured by the imaging device 2 (S12).

Specifically, 40 shots×40 shots of images of a rectangular observation region with a size of 10 cm×10 cm illustrated in FIG. 4 are captured by a phase contrast microscope to acquire one observation image. In this embodiment, it is assumed that, after a stem cell is seeded, the observation image is captured in time series at an interval of 24 hours, such as after one day, two days, three days. However, the interval at which the observation image is captured is not limited thereto. For example, the observation image may be captured at an interval of 3 hours, or may be captured while the imaging interval gradually increases in order of for example, 3 hours, 5 hours, and 8 hours. Conversely, observation image may be captured while the imaging interval gradually decreases in order of for example, 8 hours, 5 hours, and 3 hours. The imaging interval is set by the user through the input device 5 in advance and an imaging process is automatically performed on the basis of the setting of the imaging interval. It is assumed that each observation image is acquired together with the imaging time and the imaging time is associated with the observation image.

In this embodiment, the imaging device 2 captures the observation image at an optical magnification of 20 and a resolution of 1360×1024. However, the invention is not limited thereto. For example, as described above, the optical magnification and the resolution may vary depending on the feature amount of interest.

The time-series observation images captured by the imaging device 2 are output to the stem cell differentiation determination device 3 and are acquired by the observation image acquisition unit 30 of the stem cell differentiation determination device 3 (S14).

The time-series observation images acquired by the observation image acquisition unit 30 are output to the feature amount acquisition unit 31 and the feature amount acquisition unit 31 acquires at least one feature amount of the stem cell in each observation image (S16). Here, the feature amount acquisition unit 31 acquires the feature amounts as the degree of circularity of each stem cell colony in the observation image and the density of stem cells in each stem cell colony.

Then, the feature amounts which are acquired for each stem cell colony in each observation image by the feature amount acquisition unit 31 are output to the determination unit 32 and the determination unit 32 determines whether or not each stem cell colony has been differentiated, on the basis of the input feature amounts of each stem cell colony in each observation image (S18). Specifically, when the degree of circularity of the stem cell colony is equal to or greater than a predetermined threshold value and the density of the stem cells is equal to or greater than a predetermined threshold value, it is determined that the stem cell colony has not been differentiated. When the degree of circularity of the stem cell colony is less than the threshold value or the density of the stem cells is less than the threshold value, it is determined that the stem cell colony has been differentiated.

The feature amounts which are acquired for each stem cell colony in each observation image by the feature amount acquisition unit 31 are output to the change information acquisition unit 33 and the change information acquisition unit 33 acquires the imaging time of the observation image in which the feature amount of at least one stem cell colony is greater than a threshold value as the information about a change in the feature amount (S20). That is, the imaging time of the observation image in which the degree of circularity of at least one stem cell colony or the density of stem cells in the stem cell colony is less than the threshold value is acquired.

The change information acquisition unit 33 outputs the acquired imaging time and the observation image captured at the imaging time to the display control unit 34 and the display control unit 34 displays the input imaging time and observation image on the display 4 (S22).

The stem cell culture observation system according to the first embodiment acquires the information about a change in the feature amount between the observation images which are captured in time series or the information about a change in the determination result from undifferentiation to differentiation between the observation images, and outputs the information about a change in the feature amount or the information about a change in the determination result. Therefore, it possible to limit the information to be checked by the culturist, which makes it possible for the culturist to effectively and accurately check undifferentiation and differentiation.

When the observation image is displayed on the display 4, the display control unit 34 may display a feature amount, such as the degree of circularity of each stem cell colony in the observation image or the density of the stem cell colonies, on the display 4, or may display the determination result of whether or not each stem cell colony has been differentiated on the display 4. As such, when the feature amount is displayed, the culturist can know the base of the determination result of undifferentiation and differentiation and it is possible to check the determination result, without depending on the skill level of the culturist.

The display control unit 34 may display the following information on the display 4, in addition to the observation image captured at the imaging time which is acquired by the change information acquisition unit 33: the observation images captured at other imaging times; the degree of circularity of a stem cell colony in the observation image; the density of the stem cell colonies in the observation image; and the determination result of undifferentiation and differentiation.

Next, a stem cell culture observation system using a second embodiment of the stem cell differentiation determination device and method and the program according to the invention will be described.

Figure 6:
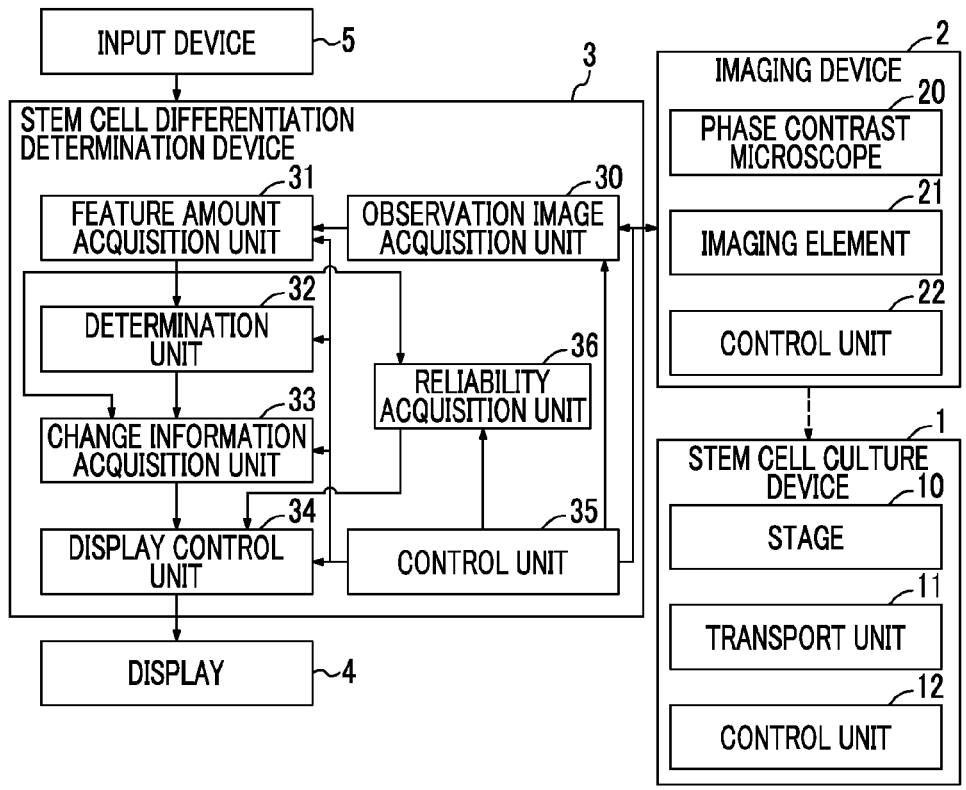
FIG. 6 is a block diagram schematically illustrating the structure of a stem cell culture observation system using a second embodiment of the stem cell differentiation determination device according to the invention.

The stem cell culture observation system according to the second embodiment differs from the stem cell culture observation system according to the first embodiment in that it further includes a reliability acquisition unit 36, as illustrated in FIG. 6. The other structures are the same as those in the stem cell culture observation system according to the first embodiment.

The reliability acquisition unit 36 acquires the reliability of the determination result for each stem cell colony or each divided region, on the basis of the feature amounts acquired for each stem cell colony or each divided region.

Specifically, for example, in a case in which the degree of circularity of each stem cell colony and the density of stem cells are acquired as the feature amounts and undifferentiation or differentiation is determined on the basis of evaluation values obtained by weighting the feature amounts, when the degree of circularity of the colony is equal to or greater than a predetermined threshold value and the density of the stem cells is equal to or greater than a predetermined threshold value, that is, when the determination result based on the degree of circularity is identical to the determination result based on the density of the stem cells, it is determined that the reliability of the determination result based on the evaluation values is high and reliability "1" is acquired.

When the degree of circularity of the colony is less than the threshold value and the density of the stem cells is less than the threshold value, the determination result based on the degree of circularity is identical to the determination result based on the density of the stem cells. Therefore, it is determined that the reliability of the determination result based on the evaluation values is high and reliability "1" is acquired.

When the degree of circularity of the colony and the density of the stem cells are values other the above-mentioned values, that is, when the determination result based on the degree of circularity is contrary to the determination result based on the density of the stem cells, it is determined that the reliability of the determination result based on the evaluation values is low and reliability "0" is acquired.

In the above description, two levels of reliability are acquired. However, the reliability is not limited to two levels. For example, three or more levels of reliability may be acquired. Specifically, the difference between the degree of circularity of the colony or the density of the stem cells and the threshold value may be acquired and the reliability may be set such that it decreases as the difference increases and increases as the difference decreases.

A reliability acquisition method when undifferentiation and differentiation are determined on the basis of the evaluation values calculated from the degree of circularity of the colony and the density of the stem cells has been described above. However, the invention is not limited thereto. For example, when undifferentiation and differentiation are determined on the basis of one feature amount, the reliability of the determination result may be acquired on the basis of the difference between the feature amount and the threshold value.

The reliability of the determination result for each stem cell colony or each divided region acquired by the reliability acquisition unit 36 is output to the display control unit 34. Then, when displaying the observation image in which the feature amount or the determination result has changed, the display control unit 34 preferentially displays the image of the stem cell colony or the divided region with low reliability, on the basis of the input reliability.

Figure 7:
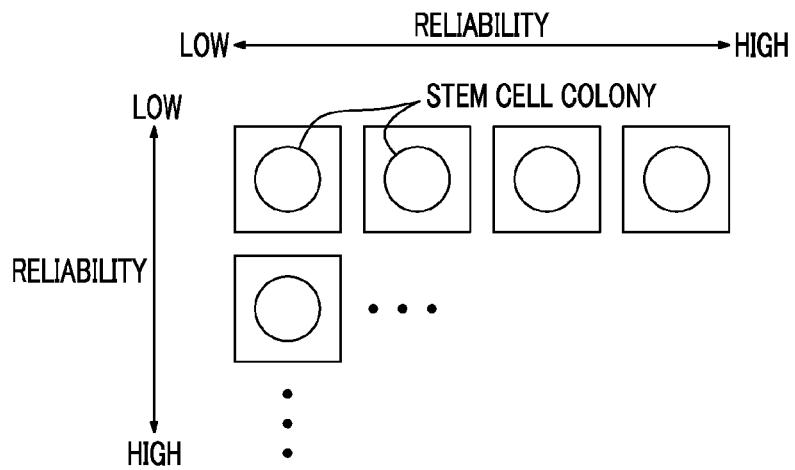
FIG. 7 is a diagram illustrating an example in which the images of a stem cell colony are displayed so as to be arranged in a predetermined array based on the level of reliability.

As a method for preferentially displaying the image, for example, the following methods may be used; a method which sequentially switches the images of the stem cell colonies or the divided regions with low reliability and displays the images; and a method which displays the images of the stem cell colonies or the divided regions so as to be arranged in a predetermined array based on the level of the reliability, as illustrated in FIG. 7. In the example illustrated in FIG. 7, reliability increases from the upper left side to the lower right side.

The stem cell culture observation system according to the second embodiment preferentially displays the image with low reliability. Therefore, it is preferable that the culturist preferentially checks the determination result from the image with low reliability. Therefore, it is possible to effectively perform an operation of checking the determination result.

In addition, when observation images other than the observation image in which the feature amount or the determination result has changed are displayed, the image of the stem cell colony or the divided region with low reliability may be preferentially displayed, as described above.

When the image of the stem cell colony or the divided region with low reliability is preferentially displayed as described above, the content of the feature amounts used to acquire the reliability may be displayed together with the image, In the stem cell culture observation systems according to the first and second embodiments, when displaying the observation image, the display control unit 34 may display the image of the entire stem cell colony or the image of a portion of the stem cell colony.

When displaying the observation image in which the feature amount or the determination result has changed, the display control unit 34 may display about 10 observation images, which are captured before and after the imaging time when the feature amount or the determination result changes, as a moving image. As such, when the moving image is displayed, it is possible to check the trajectory of change in the determination result from undifferentiation to differentiation.

What is claimed is:
1. A stem cell differentiation determination device comprising:
an observation image acquisition unit that captures an image of an observation region including a stem cell in time series to acquire at least two observation images;

a feature amount acquisition unit that acquires at least two distinct feature amounts of the stem cell within a plurality of regions within the observation region for each observation image;

a determination unit that determines whether or not the stem cell has been differentiated within each of the plurality of regions, on the basis of the at least two distinct feature amounts;

a change information acquisition unit that acquires information about a change in the distinct feature amounts within each of the plurality of regions between the observation images captured in time series or information about a change in a determination result from undifferentiation to differentiation within each of the plurality of regions between the observation images;

an output unit that outputs the information about a change in the distinct feature amounts within each of the plurality of regions or the information about a change in the determination result within each of the plurality of regions; and a reliability acquisition unit that acquires a degree of reliability for the determination results for each of the plurality of regions, based on a result of comparing the at least two distinct feature amounts within each of the plurality of regions between each other.

2. The stem cell differentiation determination device according to claim 1, wherein the change information acquisition unit acquires, as the information about a change in the distinct feature amounts within each of the plurality of regions, at least one of information about a time when the distinct feature amounts change, the observation image in which the distinct feature amounts have changed, information about a position where the distinct feature amounts have changed in the observation region, and information for specifying a stem cell colony in which the distinct feature amounts have changed.

3. The stem cell differentiation determination device according to claim 1, wherein the change information acquisition unit acquires, as the information about a change in the determination result for each of the plurality of regions, at least one of information about a time when the determination result changes, the observation image in which the determination result has changed, information about a position where the determination result has changed in the observation region, and information for specifying a stem cell colony in which the determination result has changed.

4. The stem cell differentiation determination device according to claim 1, wherein:

the output unit preferentially outputs the observation image including the regions with low reliability.

5. The stem cell differentiation determination device according to claim 1, wherein the region is a stem cell colony region.

6. The stem cell differentiation determination device according to claim 1, wherein the region is a predetermined divided region.

7. The stem cell differentiation determination device according to claim 1, wherein the output unit outputs the distinct feature amounts for each of the plurality of regions.

8. The stem cell differentiation determination device according to claim 1, further comprising:

an imaging unit that captures the observation image, wherein the imaging unit switches an optical magnification or a resolution when the observation image is captured, depending on a set feature amount of interest.

9. The stem cell differentiation determination device according to claim 1, wherein the output unit outputs the observation image of the entire stem cell colony.

10. The stem cell differentiation determination device according to claim 1, wherein the output unit outputs the observation image of a portion of the stem cell colony.

11. The stem cell differentiation determination device according to claim 1, wherein the output unit outputs a plurality of observation images, which are captured before and after the time when the distinct feature amounts of each of the plurality of regions change or the time when the determination result for each of the plurality of regions changes, as a moving image.

12. A stem cell differentiation determination method comprising:

capturing an image of an observation region including a stem cell in time series to acquire at least two observation images;

acquiring at least two distinct feature amounts of the stem cell within a plurality of regions within the observation region for each observation image;

determining whether or not the stem cell has been differentiated within each of the plurality of regions, on the basis of the at least two distinct feature amounts;

acquiring information about a change in the distinct feature amounts within each of the plurality of regions between the observation images captured in time series or information about a change in a determination result from undifferentiation to differentiation within each of the plurality of regions between the observation images, and outputting the information about a change in the distinct feature amounts or the information about a change in the determination result; and further obtaining a degree of reliability for the determination result for each of the plurality of regions based on the result of comparing the at least two distinct feature amounts within each of the plurality of regions between each other.

13. A non transitory computer readable recording medium having stored therein a stem cell differentiation determination program that causes a computer to function as:

an observation image acquisition unit that captures an image of an observation region including a stem cell in time series to acquire at least two observation images;

a feature amount acquisition unit that acquires at least two distinct feature amounts of the stem cell within a plurality of regions within the observation region for each observation image;

a determination unit that determines whether or not the stem cell has been differentiated within each of the plurality of regions, on the basis of the at least two distinct feature amounts;

a change information acquisition unit that acquires information about a change in the distinct feature amounts within each of the plurality of regions between the observation images captured in time series or information about a change in a determination result from undifferentiation to differentiation within each of the plurality of regions between the observation images;

an output unit that outputs the information about a change in the distinct feature amounts within each of the plurality of regions or the information about a change in the determination result within each of the plurality of regions; and
a reliability acquisition unit that acquires a degree of reliability for the determination results for each of the plurality of regions, based on a result of comparing the at least two distinct feature amounts within each of the plurality of regions between each other.

14. A stem cell differentiation determination apparatus as defined in claim 1, wherein:
the reliability acquisition unit sets the degree of reliability to be higher for a case in which the determination results based on each of the distinct feature amounts are the same than for a case in which the determination results based on each of the distinct feature amounts are not the same.

\* \* \* \* \*